United States Patent [19]
Bizzio

[11] Patent Number: 5,685,360
[45] Date of Patent: Nov. 11, 1997

[54] APPARATUS FOR THE CASTING AND AUTOGENOUS WELDING OF SMALL METAL LOADS IN AN INERT ATMOSPHERE

[75] Inventor: Nickolas Bizzio, Monte-Carlo, Monaco

[73] Assignee: Peacock Limited L.C., Cheyenne, Wyo.

[21] Appl. No.: 615,915

[22] Filed: Mar. 14, 1996

[51] Int. Cl.[6] .......................... B22D 11/00; B22D 27/15
[52] U.S. Cl. .......................... 164/508; 164/256; 164/259
[58] Field of Search .......................... 164/508, 495, 164/61, 65, 66.1, 68.1, 254, 256, 136, 335, 259

[56] References Cited

U.S. PATENT DOCUMENTS

| | | |
|---|---|---|
| 5,460,218 | 10/1995 | Miwa et al. ........................ 164/65 |
| 5,524,705 | 6/1996 | Matsubara et al. ................. 164/61 |

Primary Examiner—Joseph J. Hail, III
Assistant Examiner—I.-H. Lin
Attorney, Agent, or Firm—Daniel O'Byrne

[57] ABSTRACT

The casting apparatus has a case defining a casting chamber having an open front provided with a door, and a crucible locatable in the chamber for containing metal loads to be cast. An electrode extends through a wall of the chamber and is connectable to a power source for the formation of an electric arc between the electrode and the load in the crucible. A coupling connects the inside of the chamber to a source of pressurized inert gas or to a vacuum pump. A tubular element for containing a mold is removably accommodatable in the chamber at an opening, which is connected to the atmosphere by a vent valve. A fluid-activated jack is provided for tilting the case for pouring molten metal, from the crucible to the mold contained in the tubular element.

23 Claims, 7 Drawing Sheets

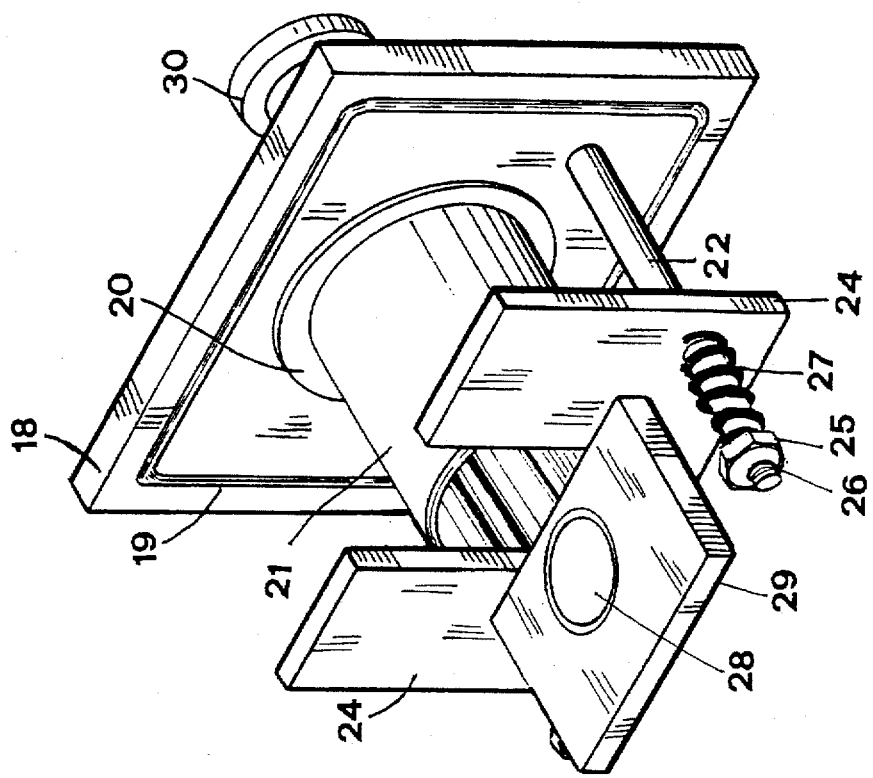
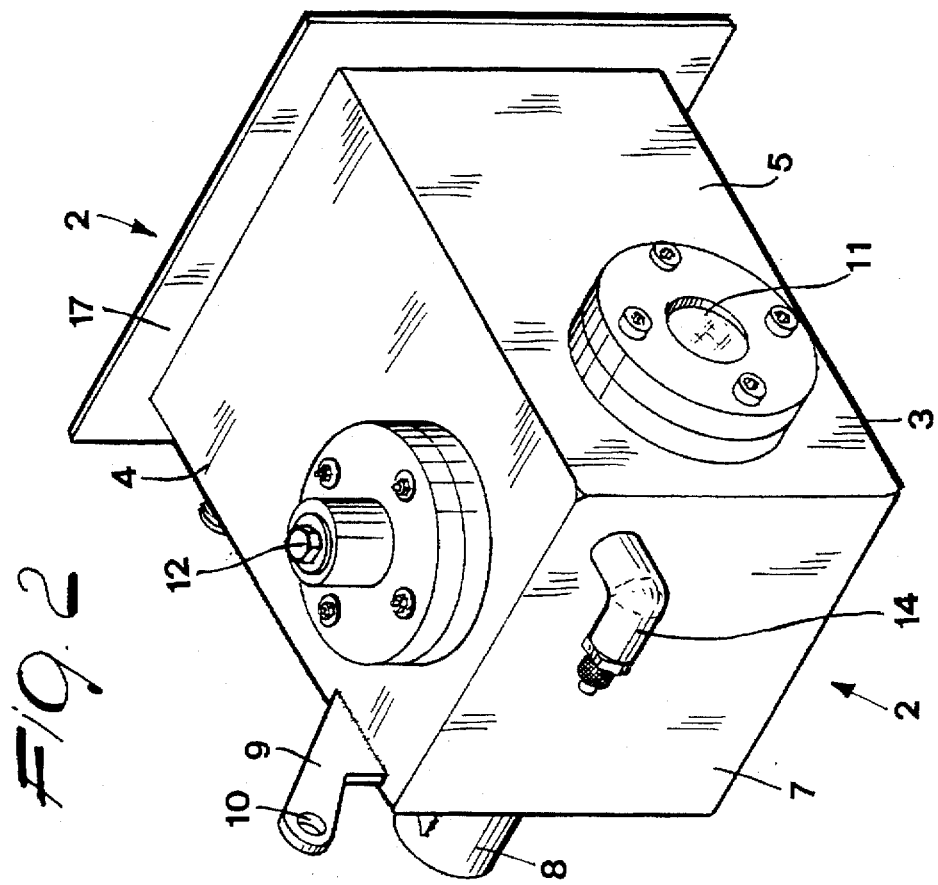

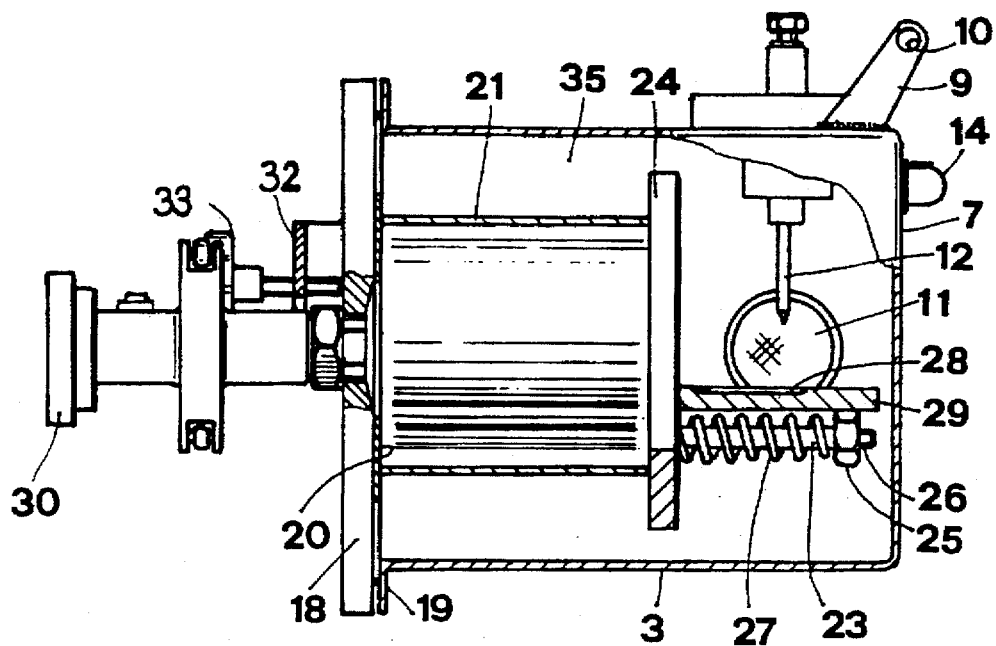
Fig. 4
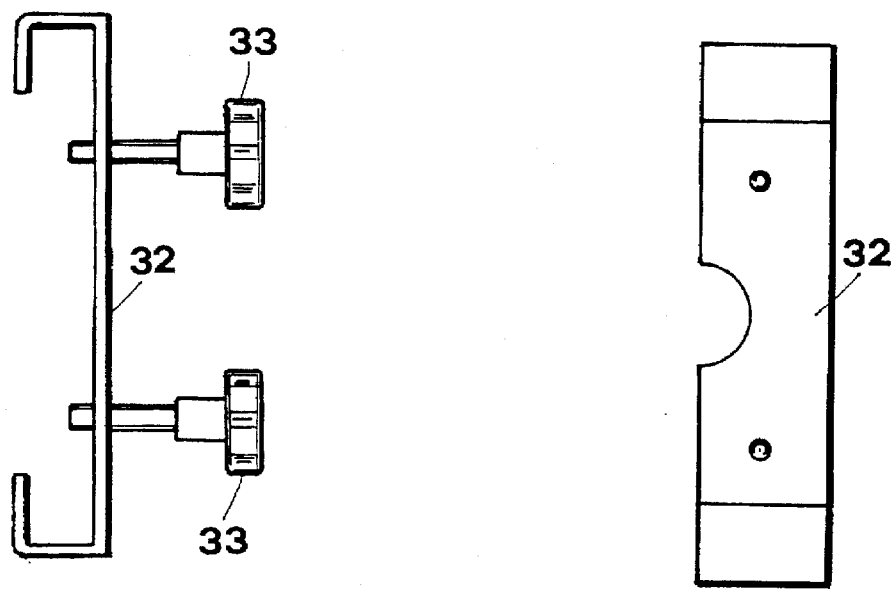
Fig. 5
Fig. 6

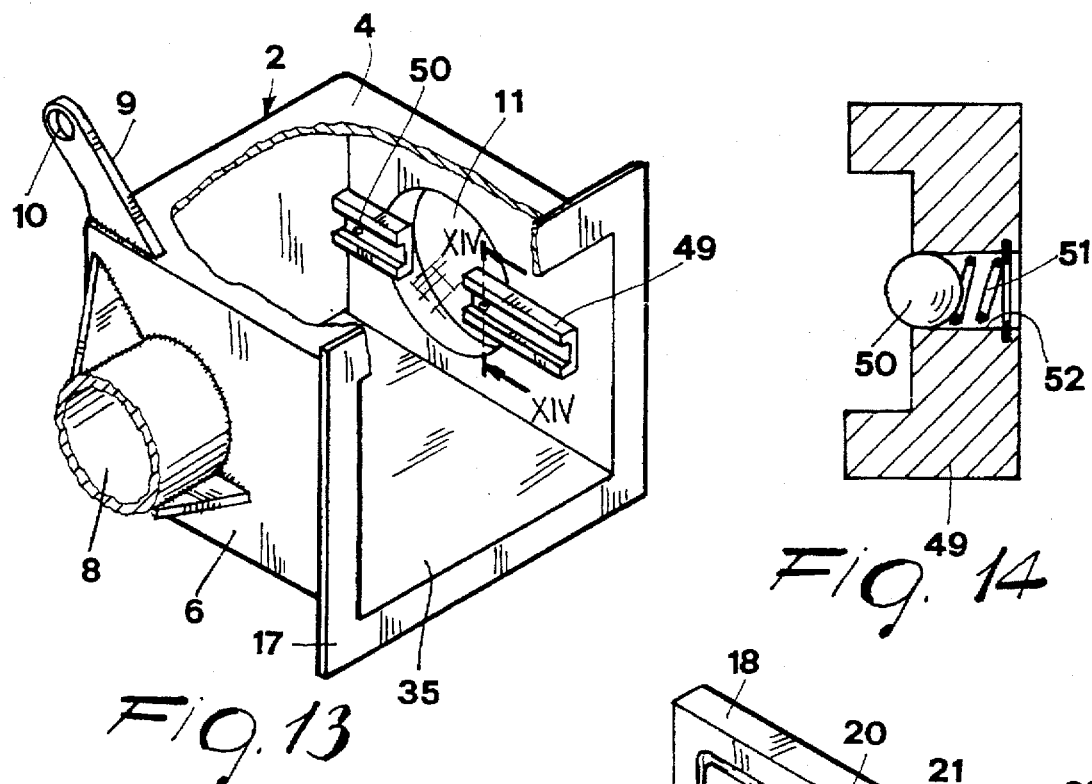
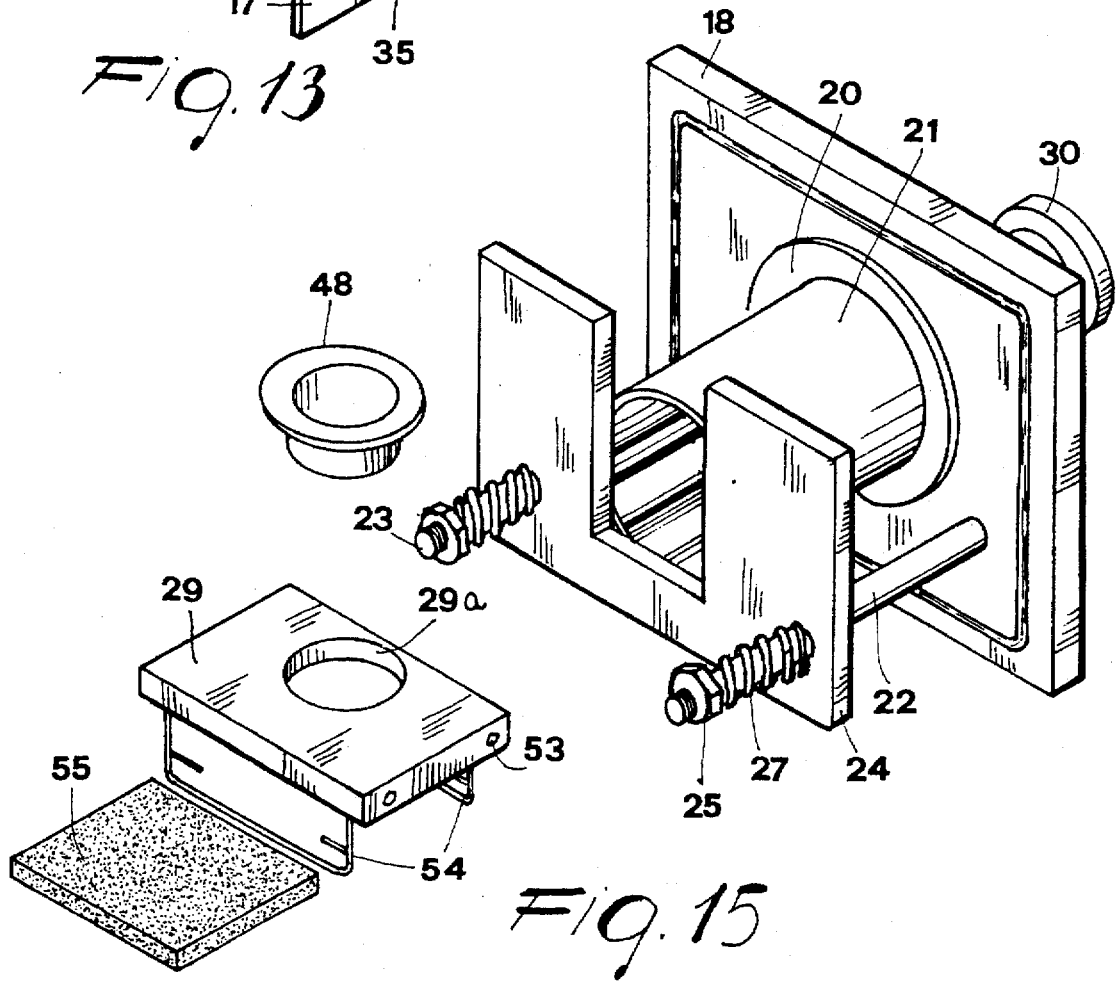

5,685,360

APPARATUS FOR THE CASTING AND AUTOGENOUS WELDING OF SMALL METAL LOADS IN AN INERT ATMOSPHERE

BACKGROUND OF THE INVENTION

The present invention relates to an apparatus for the casting and autogenous welding of small metal loads in an inert atmosphere for obtaining dental prostheses, jewels, and the like.

In EP-A1-0 651 220, a method and an apparatus for casting relatively small metal loads in an inert atmosphere have already been proposed in which there is a melting chamber and a casting chamber that are mutually rigidly associated and adjacent but are separated by a dividing wall. The melting and casting chambers can be tilted with respect to the horizontal by rotation about a transverse axis. The melting chamber is provided with an arc electrode and a copper crucible, whereas the casting chamber accommodates a mold, so that once the electric arc has been ignited and the melting of the metal load—constituted by a titanium pellet—has been produced in the crucible, it is sufficient to perform a partial rotation about said transverse axis to cause casting, i.e., the transfer of the molten metal load into the mold inside the casting chamber. Both melting and casting occur in an inert environment, after producing a vacuum inside the two chambers, to prevent the formation of unwanted oxides, which would compromise the quality of the casting and of the final component, which may be, e.g., a metal support for a dental prosthesis or a jewel or the like.

The mold in the casting chamber is kept in position within a removable tubular element that must be loaded hermetically inside the casting chamber and therefore requires the presence of two vacuum-tight gaskets, i.e., a gasket at each end of the tubular element. Of course, it may occur that due to an imprecise positioning of the tubular element against one of the gaskets, the suction flow for forming the vacuum inside the casting chamber may not be unidirectional inside the tubular element, and this can lead to the imperfect evacuation of the oxygen. The presence of any oxygen adversely affects the quality of the castings that are obtained.

SUMMARY OF THE INVENTION

An aim of the present invention is to provide an apparatus for melting small metal loads in an inert environment that is capable of ensuring the obtainment of defect-free castings.

Another object of the present invention is to provide an apparatus which is capable of casting not only titanium but also a large number of alloys of noble metals, such as chrome, nickel, palladium, cobalt, vanadium, and the like.

A further object of the present invention is to provide a casting apparatus that, if necessary, can also perform autogenous welds on the cast parts that are obtained.

With this aim and these and other objects in view, there is provided a casting apparatus according to the invention, which comprises:

- a metallic box-like case defining a melting and casting chamber, having at least one side wall and two end walls and mounted for rotation between a loading position, in which its two end walls are substantially aligned horizontally, and a casting position, in which one of said end walls constitutes the bottom and the other one constitutes the ceiling of said chamber;
- at least one opening/closing door for said chamber;
- a crucible locatable inside said chamber for accommodating a metal load to be cast;
- at least one electrode extending hermetically through a wall of said chamber and externally connectable to a source of electric power to form an electric arc between the electrode and the load in the crucible;
- a coupling means for connecting the inside of said melting and casting chamber either to a source of a pressurized inert gas or to a source of vacuum;
- a tubular element for containing a mold, which is removably insertable in said chamber;
- engagement means for an end of the tubular element that is directed toward said bottom wall of the chamber;
- means for the formation of a seal between said engagement means and said end of said tubular element that is engaged by said means; and
- at least one opening that passes through at least one of the walls of said chamber and through which the inside of said tubular element can be connected to the outside of said chamber by virtue of a check valve.

BRIEF DESCRIPTION OF THE DRAWINGS

Further aspects and advantages of the present invention will become apparent from the following detailed description of some currently preferred examples of embodiment thereof, given only by way of non-limitative illustration with reference to the accompanying drawings, wherein:

FIG. 2 is a perspective view, in slightly enlarged scale, of a containment case;

FIG. 3 is a perspective view of a bottom plate for the hermetic closure of the case of FIG. 1, provided with removable fixing means for the tubular element for containing the casting pattern;

FIG. 4 is a lateral elevation view, with parts shown in cross-section, of a casting apparatus according to the invention, assembled and ready for use;

FIGS. 5 and 6 are, respectively, a top view and a side view of a bracket for the removable mutual fixing of the case and of the bottom plate;

FIG. 13 is a perspective view, with parts shown in cross-section and in enlarged scale, of the case of the casting apparatus of FIG. 12;

FIG. 14 is an enlarged-scale sectional view, taken along the plane XIV—XIV of FIG. 13;

FIG. 15 is an exploded view of the internal components and of the closure bottom plate for the case of FIG. 12.

In the accompanying drawings, identical or similar parts or components have been designated by the same reference numerals.

DESCRIPTION OF THE PREFERRED EMBODIMENTS

Figure 1:
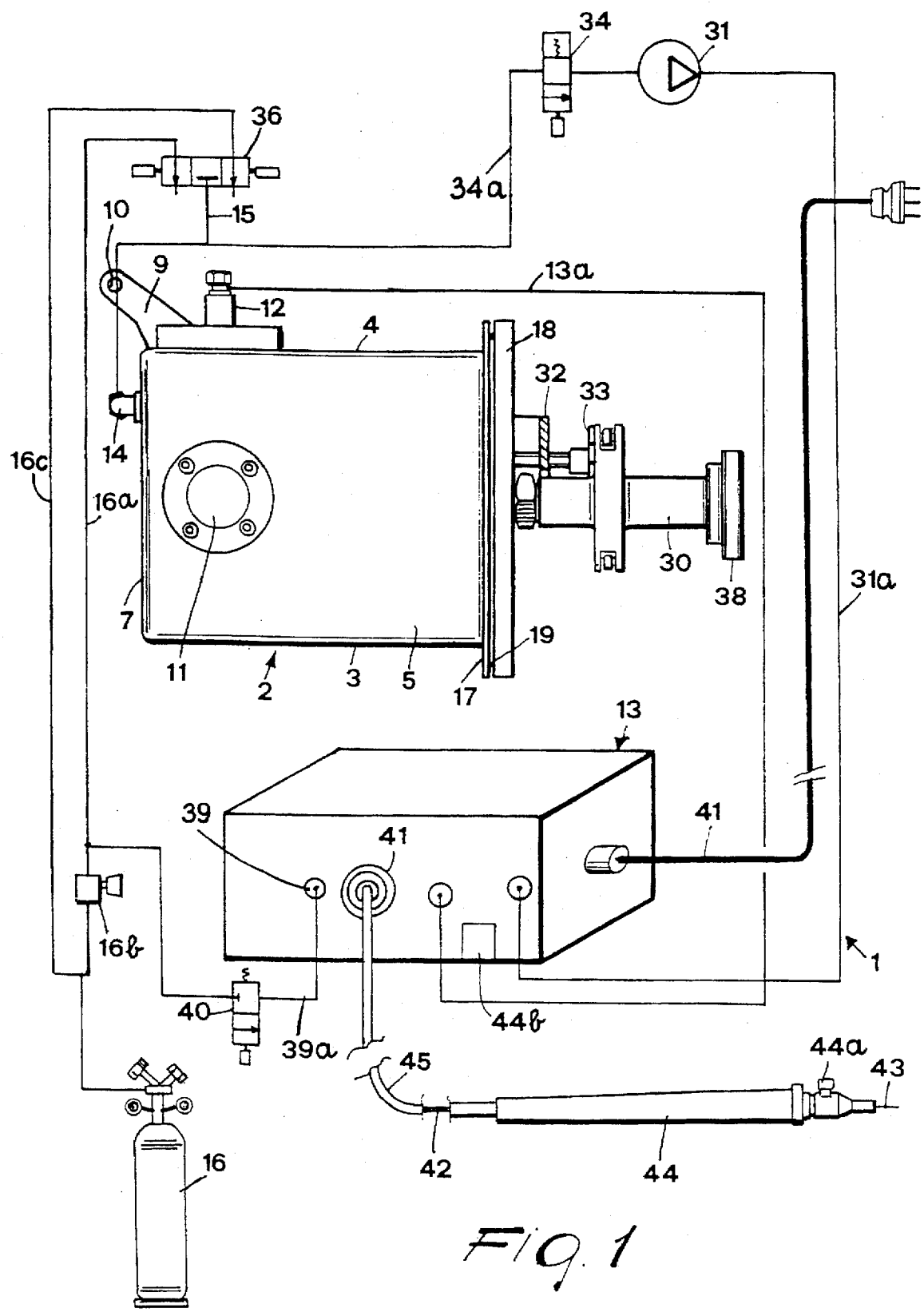
FIG. 1 is a schematic lateral elevation view of a casting and autogenous welding apparatus according to the invention.

Initially with reference to FIGS. 1 to 6, a casting apparatus, generally designated by the reference numeral 1, according to the invention is constituted by a metallic box-like case 2 that has a bottom wall 3, an upper wall 4, two side walls 5 and 6, and a rear wall 7 defining a melting and casting chamber that is open at the front. The box-like case or chamber 2 is meant to be mounted, during use, so that it can rotate about the axis of a mounting bush 8 which is rigidly coupled, for example butt-welded, to one of the side walls with a rotation axis that is normal to said wall and mounted for rotation about a fixed pivot of a supporting structure (not shown in the drawings).

In order to make the chamber 2 rotate about the axis of the bush 8, there is a lug 9 that is spaced from the bush 8. The lug protrudes for example from the upper wall 4 to which it is welded, and has an articulation hole or loop 10 whose axis is parallel to that of the bush 8. The lug 9, at the hole or loop 10, is articulated to a suitable actuation means, such as a linear actuator, for example a fluid-driven piston-and-cylinder unit (not shown in the drawings), which by acting on the lug 9 forces the case 2 to perform angular tilting strokes about the axis of the bush 8.

The side wall that lies opposite to the one affected by the mounting bush 8 has an inspection window 11, whereas the upper wall is crossed hermetically by an electrode 12 for the formation of an electric arc, which can be connected externally, by virtue of a cable 13a, to a source of electric power with the interposition of a suitable control unit 13, commonly known as a generator.

The rear wall 7 instead has a nipple or union 14 for connection, by means of a duct 15, to a source of inert gas, such as an argon cylinder 16, as also specified hereinafter, whereas the front part of the box-like case is fully open and is affected by a peripheral flange 17 that runs all around the internal opening.

The front of the box-like case 2 can be closed by a removable closure bottom plate 18, also made of metal, which in the tilted or casting position of the case 2 constitutes the end wall of the melting and casting chamber and has dimensions which are, for example, equal to those of the peripheral flange 17. A peripheral groove is formed on the inside face of the bottom plate 18, i.e., on the face that is, directed, during use, toward the box-like case 2; said groove follows the contour of the internal opening of the box-like case and acts as a seat for a sealing gasket 19.

In its central part, the closure bottom plate 18 has a through hole (not shown in the drawings), around which it is possible to provide a peripheral seat for a relatively wide annular sealing gasket 20. A cylindrical element 21 can abut in a cantilevered manner against the gasket 20; said element acts as a containment seat for a casting mold (which is not shown and is per se known in the state of the art).

For this purpose, removable means are provided for fixing the cylindrical element 21 in position, which in this embodiment are formed by two parallel sliding pins or guides 22 and 23, which extend, in a cantilever manner, from the inside face of the bottom plate 18. A cross-member 24, is slideably mounted on the two guides 22 and 23, and an end retainer, constituted for example by a nut 25, is screwed onto the threaded end 26 of each respective guide. A helical spring 27 is wound around each pin 22 and 23 between the cross-member 24 and the nut 25 in contrast with the sealing means for said tubular element.

The cross-member 24 can assume various configurations, but in any case it must rest against the edge of the cylindrical seat 21 and must not cover the entire opening of said seat.

As shown more clearly in FIGS. 3 and 4, the cross-member 24, in addition to acting as an element for retaining the cylindrical seat 21 in a cantilevered position, also supports a melting crucible 28 that is formed in a copper plate 29.

At its outer face, the bottom plate 18 can be connected, by virtue of a union 30, to a source vacuum, such as an electric vacuum pump 31 that is capable of producing, inside the box-like case 2, a vacuum of at least 1/100 bar and is connected to the generator 13 means of a cable 31a.

The size of the entire assembly supported by the bottom plate 18 is such that once it is inserted in the box-like case 2, the crucible 28 is centered and at a short distance below the tip of the electrode 12.

In order to keep the bottom plate 18 pressed hermetically against the flange 17, it is possible to adopt various types of locking means, constituted for example by a bracket 32 (FIGS. 5 and 6) having ends which are folded in the same direction, so that it can be inserted from above around the edges of the bottom plate 18 and the flange 17. The bracket, on the side that lies opposite to the one where its ends are folded, is provided with a pair of clamps 33, each of which is constituted by threaded stem that can be screwed into a corresponding threaded hole of the bracket and is actuated by a respective knob. Once the bracket 32 has been inserted in position, by acting on the clamps 33 it is possible to detachably lock the bottom plate 18 and the flange 17 against each other, so as to ensure a hermetic seal.

If a metal load to be melted has been provided in the crucible 28, and if a casting mold, for example for a dental prosthesis, provided with venting and air evacuation holes as is conventional in the art, has been located in the cylindrical seat 21, it is possible to perform a casting process that occurs according to the following operating sequence.

First of all, a vacuum between 1/10 and 1/100 bar is produced inside the box-like case, by opening an electric valve 34 that is located on a duct 34a that is connected to the duct 15 and to the electric vacuum pump 31. In this manner, the air inside the chamber 35 within the box-like case 2 and in the cylindrical element 21 and in the casting pattern contained therein is evacuated. Then, once the preset vacuum level has been reached, the electric valve 34 closes so as to interrupt the connection between the chamber 35 and the vacuum source 31, and then an electric valve 36 is opened between the cylinder 16 and the duct 15, for feeding argon to the chamber 35, through a low-pressure line 16a that is provided with a pressure regulator 16b and a line 16c at a relatively high pressure. The low-pressure argon thus penetrates the recesses and interstices, emptied beforehand, of the casting mold that lies inside the cylindrical seat 21, and completely fills the chamber 35.

At this point, the control unit 13 ignites the electric arc between the tip of the electrode 12 and the metal load to be melted which is present in the crucible 28 in order to melt the metal. Once melting has occurred, after a preset time the control unit emits a control impulse to activate the actuation means (fluid-activated jack) in order to tilt the box-like case 2, and therefore the chamber 35, with respect to the vertical, causing a partial rotation of the box-like case 2 about the axis of the bush 8 by acting on the lug 9, in order to pour the molten metal from the crucible 28 into the mold inside the cylindrical seat 21.

The control unit 13 then closes the branch of the electric valve 36 that is connected to the low-pressure line 16a and opens its other branch 16c at high pressure, which bypasses the pressure regulator 16b to feed into the chamber 35, and therefore into the mold inside the cylindrical element 21, argon at a relatively high flow-rate and pressure, resorting if required to a slave cylinder (not shown), in order to stabilize the casting inside the mold. The argon thus fed into the chamber 35 is discharged in a controlled manner into the atmosphere through a membrane discharge valve 38 that is provided on the union 30.

It is evident that with the above described casting apparatus, the melting and casting chamber are interconnected and are always in the same conditions in terms of ambient atmosphere, pressure and/or vacuum. In other words, they constitute a single space that lies inside the box-like case 2, where with a single annular sealing gasket 20 it is possible to ensure airtightness between the chamber 35 and the outside environment both for the vacuum and for the inert gas.

Of course, management of the operating sequence can be manual or preferably assigned to a control device based on a program or on an electronic control device in the control generator 13.

The casting apparatus 1 is also provided with an inlet 39 for a manifold, preferably located in the generator 13, that is reached by a duct 39a that arrives from the line 16a with the interposition of an electric shut-off valve 40 for the inert gas fed by the cylinder 16 through the pressure reduction unit 16b.

The manifold has an outlet 41 from which there branch off a shielded electric cable 42, which supplies an autogenous-welding electrode 43 provided with a handle 44 and with a control button 44a, and an external duct 45 for the inert gas, which is coaxial to the electric cable 42 and feeds argon to a peripheral annular interspace that lies proximate to the tip of electrode 43 to allow to perform small autogenous welds in an inert atmosphere, by virtue of the flow of argon gas around the electrode 43, but in ambient conditions.

This achieves the advantage that the welds are produced in pulses (spot welding) by pressing a pedal or the button 44a and by providing for the presence of a timer 44b, for example a 200–300 msec timer. Melting and cooling occur within an argon jet, which keeps the entire system in an inert environment, while overheating phenomena are avoided by virtue of the fact that these are spot welds.

Indeed, by opening the valve 40, since the electric valve 36 is closed, argon flows from the cylinder 16 along the line 39a into the inlet 39 for the manifold 38 and then into the duct 45 toward the tip of the electrode 43. One can thus use the casting apparatus 1 in a simple and practical manner even to perform welding operations on castings, working in ambient conditions, without having to resort to a specifically equipped hermetic welding chamber filled with inert gas.

Figure 7:
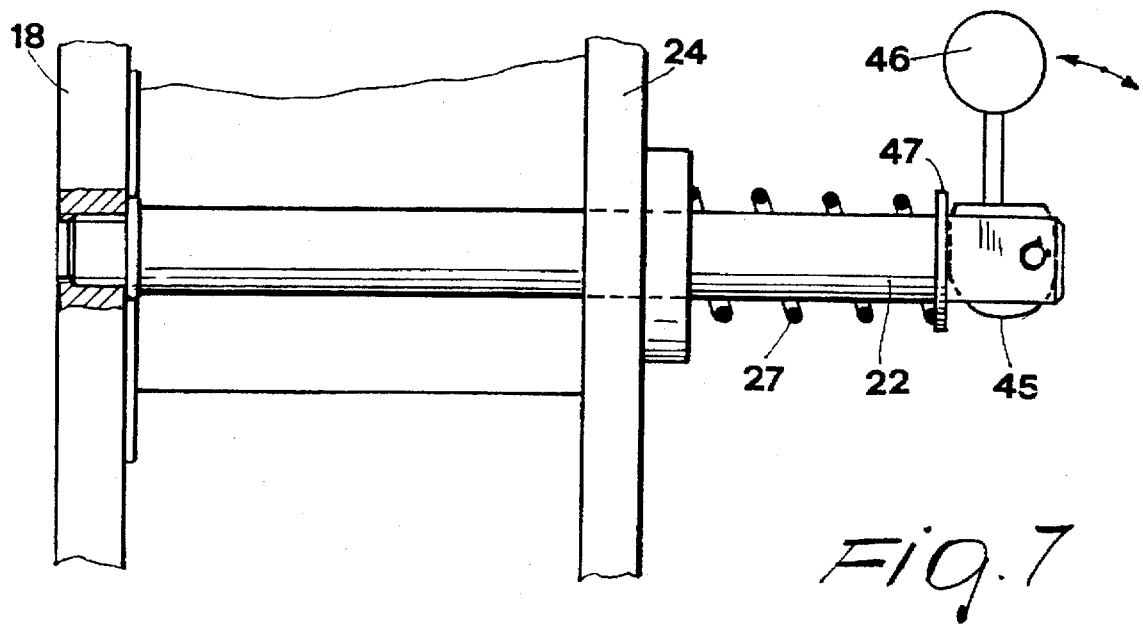
FIG. 7 is a partial lateral elevation view, with parts shown in cross-section, of a further embodiment of means for removably fixing the tubular element to the bottom plate.
Figure 8:
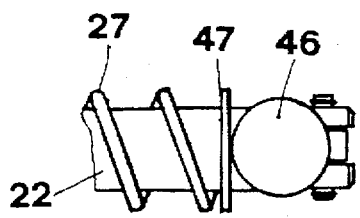
FIG. 8 is a partial plan view of a detail of FIG. 7.
Figure 9:
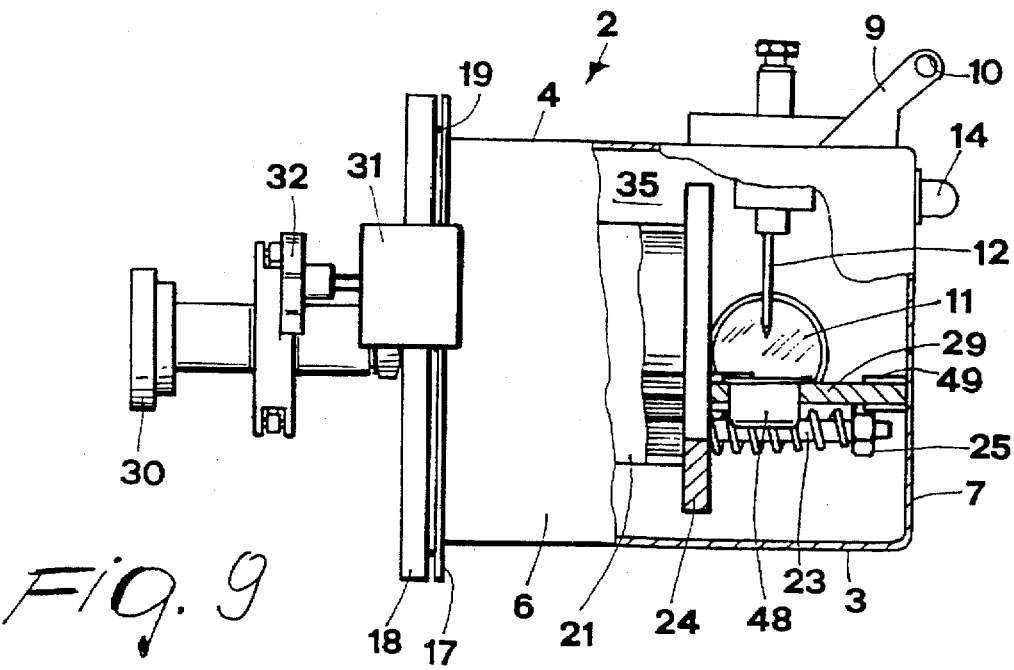
FIG. 9 is a lateral elevation view, with parts shown in cross-section, of another embodiment of a casting apparatus.
Figure 10:
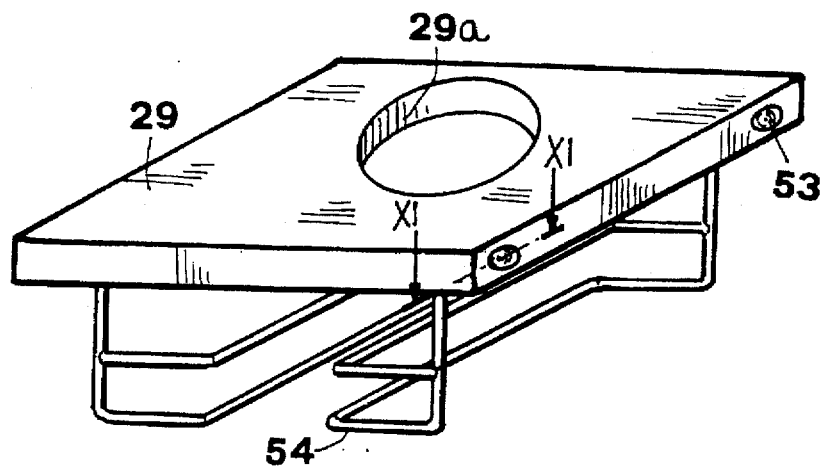
FIG. 10 is an enlarged-scale perspective view of a supporting structure for a crucible-supporting plate of the casting apparatus of FIG. 9.
Figure 11:
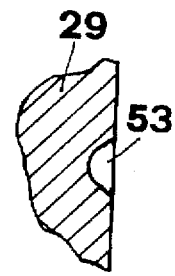
FIG. 11 is an enlarged-scale sectional view of a detail, taken along the plane IX—IX of FIG. 10.
Figure 12:
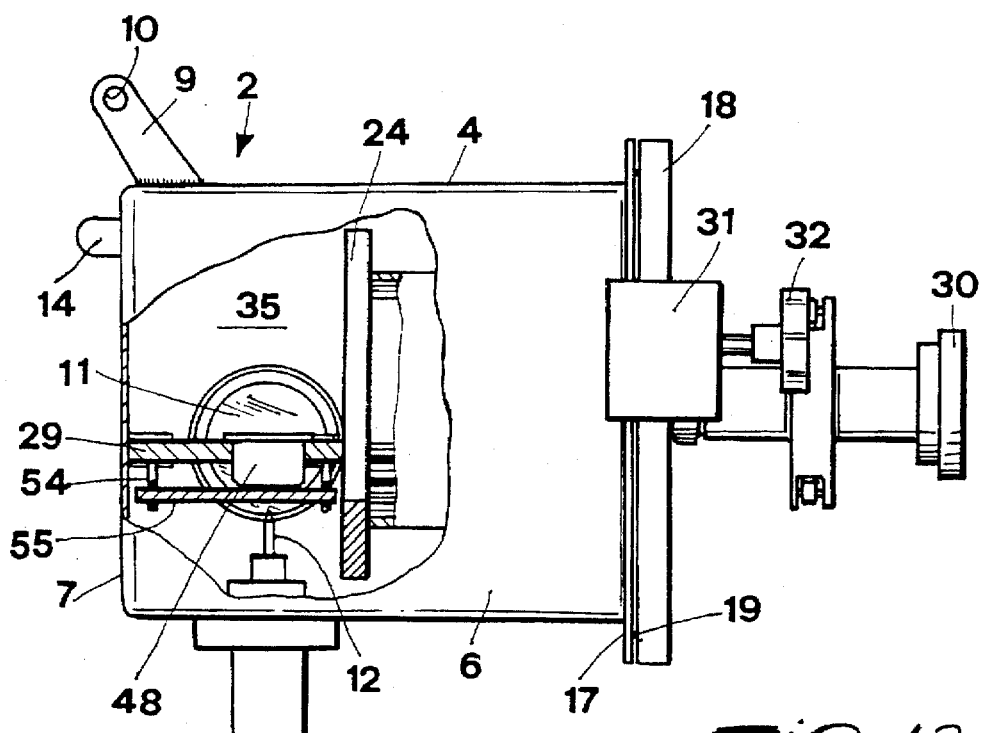
FIG. 12 is a lateral elevation view, with parts shown in cross-section, of another example of embodiment of the casting apparatus according to the invention.

In the embodiments illustrated in FIGS. 7 to 9, instead of the nuts 25 it is possible to provide an eccentric device 45 that can be actuated by an actuation lever 46 and is suitable to engage slidingly with a ring 47 for the abutment of the spring 27 that is mounted slidingly on each pin 22 and 23. With this arrangement, locking in the active position and release of the cross-member 24 in abutment against the cylindrical seat 21 are facilitated.

Furthermore, the crucible is not obtained in the plate 29 but is constituted by an appropriate copper or graphite container 48 that can be removably seated in an appropriate hole 29a that is provided in the plate 29, which is supported inside the chamber 35 by lateral bracket-like guides 49 supported by the side walls of the box-like case 2. When the bottom plate 18 is removed from the box-like case 2, the mold and the corresponding cylindrical seat 21 are removed but the crucible 48 is not removed.

FIGS. 10 to 15 illustrate another embodiment, in which the electrode 12 is mounted through the bottom wall 3, extending from the bottom upward. For this purpose, the plate 29 can be inserted on guides 49, inside the chamber 35, and is provided with retention means, such as for example means with a ball 50 that is loaded by a spring 51 inside a hole 52 of the guides 49, which cooperates with a recess 53 on a side of the plate 29 to position it precisely inside the chamber 35.

Furthermore, the plate 29 is provided, in a downward region, with a guiding and supporting system 54 for a graphite briquette 55 that acts as a protective but heat-conducting shield between the electrode 12 and the crucible 48 in order to prevent said crucible from being perforated owing to repeated use.

Figure 16:
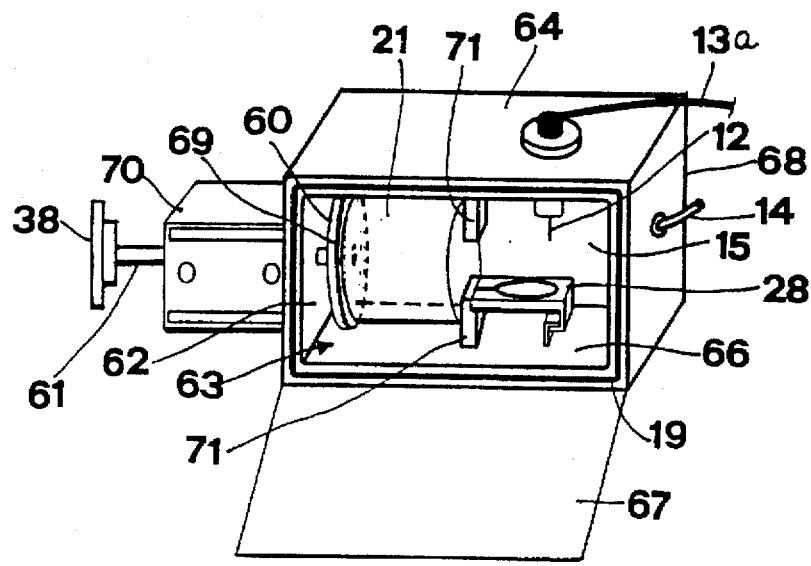
FIGS. 16 and 17 are schematic views of another embodiment of a casting apparatus according to the invention, shown in two operating positions, respectively for loading the tubular element that contains a mold and for the extraction thereof after casting, i.e., after the overturning of the melting and casting chamber.
Figure 17:
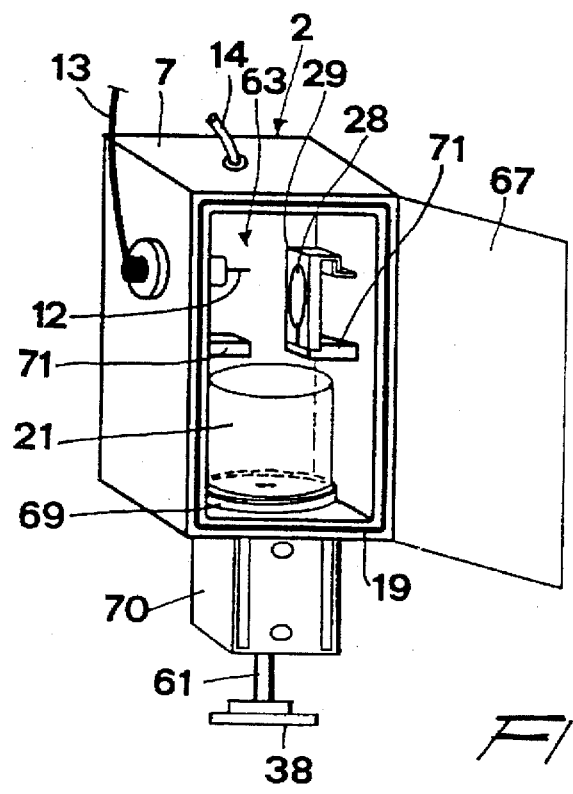

FIGS. 16 and 17 are views of a further example of an embodiment of a casting apparatus according to the present invention, wherein the engagement means for the end of the tubular element are constituted by a pan 60 that has a hollow stem 61, ends externally with a discharge membrane valve 38, and is slidingly mounted hermetically through the fixed end wall 62 of a melting and casting chamber 63. The chamber 63 is delimited by three fixed side walls 64, 65, and 66, by a side wall 67 that can be opened by virtue of a hinged door 67, and by two end walls: the bottom wall 62 and the facing top wall 68. The face of the pan that is directed toward the inside of the chamber 63 is preferably affected by an annular seat for accommodating a sealing gasket 69, against which an end of a tubular element 21 for accommodating a casting pattern (not shown in the drawings) can abut.

The position or level of the pan 60 inside the chamber 63 can be changed or adjusted by providing any suitable means for the actuation of the pan, such as a pneumatic double-action jack 70 or a rack system or another equivalent means that acts on the stem 61 to move the pan 60 between an inactive position that is close or adjacent to the bottom wall 62, at which it is easily possible to load or remove a tubular element 21, and an active position, in which said tubular element is supported and pressed against one or more abutments 71 which extend, for example in a cantilever manner, from one or more side walls of the melting and casting chamber 63.

At one of said abutments 71 it is possible to provide any suitable system for the removable mounting of a copper melting crucible 28 provided with a recess 29 that is located at an electrode 12.

In the configuration for loading the melting and casting chamber 63, shown in FIG. 16, by opening the door 67 that cooperates with a peripheral sealing gasket 19 it is possible to both position the tubular element 21 that contains a casting mold on the pan 60 and to place a load (usually in the form of a disk) of metal, such as titanium, in the crucible 28. Once the melting of the metal load in an inert environment has been achieved, after producing a vacuum—as explained above—and after filling the chamber 63 and the pattern in the tubular element 21 with inert gas (argon), the melting chamber itself is tilted to pour the molden metal into the mold; simultaneously, a considerable flow of inert gas is fed and, in addition to maintaining an oxygen-free inert atmosphere, helps to force and entrain the molten metal into the cavities of the mold contained in the tubular element 21; said flow can discharge externally in a controlled manner through the tubular element 21 itself, the pan 20, its hollow stem 61, and the discharge valve 38.

The above described casting and welding apparatus is susceptible to numerous modifications and variations within the protective scope defined by the claims.

It is evident that it allows the operate substantially only with three electric valves and with a pressure regulator and without the need to provide separate melting and casting chambers.

What is claimed is:

1. Casting apparatus, comprising:
   a metallic box-like case defining a melting and casting chamber and having at least one side wall and two end walls and mounted for rotation between a loading position, in which said two end walls are substantially aligned horizontally, and a casting position, in which one of said end walls constitutes a bottom and the other one of said end walls constitutes a ceiling of said chamber;
   at least one opening/closing door for said chamber;
   a crucible located inside said chamber for accommodating a metal load to be cast;
   at least one electrode extending hermetically through a wall of said chamber and externally connectable to a source of electric power for form an electric arc between the electrode and the load in the crucible;
   a coupling means for connecting the inside of said melting and casting chamber either to a source of a pressurized inert gas or to a source of vacuum;
   a tubular element for containing a mold, said tubular element being removably insertable in said chamber;
   engagement means for an end of the tubular element that is directed toward said bottom of the chamber;
   means for forming a seal between said engagement means and said end of said tubular element that is engaged by said means; and
   at least one opening that passes through at least one of the walls of said chamber and through which the inside of said tubular element can be connected to the outside of said chamber by virtue of a check or vent valve.

2. Apparatus according to claim 1, wherein said engagement means comprise means for removably fixing in position said tubular element against said supporting seat and said sealing means.

3. Apparatus according to claim 2, wherein said crucible is supported by said removable fixing means in a cantilevered position.

4. Apparatus according to claim 2, wherein said removable fixing means comprise at least two guide elements extending from the inside face of said closing bottom plate, a transverse element slideable along said guide elements and abutting against part of an end of said tubular element, an end retainer or shoulder on each guide, and means for elastic loading between a cross-member and each end retainer.

5. Apparatus according to claim 4, wherein said elastic loading means can be actuated by an eccentric device.

6. Apparatus according to claim 4, wherein said crucible is formed in a recess provided in a plate-like element supported by said transverse element.

7. Apparatus according to claim 1, comprising a detachable closure bottom plate for said at least partially open wall, which has means for hermetic closure and a through opening, which is surrounded by sealing means at the face of the bottom plate directed towards said chamber and connected to said check or vent valve at its opposite face.

8. Apparatus according to claim 1, wherein said crucible comprises a plate-like element with an accommodation hole or supporting frame, guides for said plate-like element or supporting frame that are arranged within said box-like case, and a copper or graphite container that can be seated in said plate or frame.

9. Apparatus according to claim 8, wherein said plate-like element or supporting frame is provided with means for retention in inserted position in the box-like case.

10. Apparatus according to claim 8, wherein said retention means comprise at least on ball that is seated in a hole in said supporting and sliding guides and is loaded by an elastic means to cooperate with a respective recess formed on a side of said plate-like element or supporting frame.

11. Apparatus according to claim 10, wherein said electrode is directed from the bottom upward at the crucible.

12. Apparatus according to claim 11, wherein said plate-like element or supporting frame comprises lower guiding and supporting means, a graphite briquette that acts as protective but heat-conducting shield between the electrode and said container made of refractory material or graphite, and can be removably seated in said lower guiding and supporting means.

13. Apparatus according to claim 1, wherein said removable means for hermetic closure between said removable bottom plate and said at least partially open wall comprise a flange that runs peripherally around said at least partially open wall, against which said bottom plate abuts, and clamp means for mutually locking said flange and said bottom plate.

14. Apparatus according to claim 1, wherein said engagement means for an end of the tubular element comprise a pan movably mounted at said bottom wall of said chamber; actuation means for said pan, for moving said pan between from an inactive position, adjacent to said end wall, and an active position in abutment against said tubular element; and tubular duct means connecting the inside of said tubular element to said discharge valve.

15. Apparatus according to claim 14, wherein said tubular-duct means comprise at least one hollow stem for said pan that is mounted so that it can move slidingly and hermetically through the bottom wall of said chamber.

16. Apparatus according to claim 15, wherein the face of said pan that is directed toward the inside of the chamber is affected by an annular seat for accommodating a sealing gasket, against which an end of a tubular element for accommodating a casting mold can abut.

17. Apparatus according to claim 15, wherein said melting and casting chamber is delimited by three fixed side walls, by a side wall that can be opened like a hinged door, and by two end walls.

18. Apparatus according to claim 1, wherein said discharge means connected to said opening in the bottom plate comprise a membrane check valve.

19. Apparatus according to claim 1, comprising a program-based control and monitoring unit.

20. Apparatus according to claim 19, wherein said coupling means for connecting the inside of the box-like case to said source of a pressurized inert gas comprises two parallel supply lines, a pressure regulator on one of said supply lines, and an electric valve with two inlets and an outlet that is connected to the inside of said box-like case, said electric valve being driven by said control and monitoring unit.

21. Apparatus according to claim 20, wherein said means for coupling to a vacuum source comprise an electric valve that can be driven by said control and monitoring unit.

22. Apparatus according to claim 1, comprising an autogenous-welding electrode, an annular chamber that is delimited by a jacket for partially containing said electrode, a cable for supplying electric power to said electrode, a duct for feeding inert gas into said annular chamber, which receives inert gas from said inert gas source with the interposition of an electric valve that is driven by said control and monitoring unit and is placed between said source and said control unit, and a time-controlled unit for controlling the supply of electric power to said electrode.

23. A casting apparatus, comprising: a metallic box-like case defining a casting chamber and having an open front provided with a door and a crucible located in the chamber for containing metal load; a tubular element for containing a casting mold, which is removably accommodatable in the chamber; and at least one opening connecting the tubular element to the atmosphere by a vent valve.

* * * * *